United States Patent [19]

Nigro

[11] 4,048,998
[45] Sept. 20, 1977

[54] TAMPON INSERTER
[75] Inventor: Louis V. Nigro, Saugus, Mass.
[73] Assignee: The Gillette Company, Boston, Mass.
[21] Appl. No.: 659,489
[22] Filed: Feb. 19, 1976
[51] Int. Cl.² ............................................ A61F 15/00
[52] U.S. Cl. ................................................. 128/263
[58] Field of Search .............. 128/263, 264, 285, 270, 128/130

[56] References Cited
U.S. PATENT DOCUMENTS

| 702,570 | 6/1902 | Lohlein | 128/263 |
| 2,155,285 | 4/1939 | Wilkerson | 128/263 X |
| 3,090,385 | 5/1963 | Brecht | 128/263 |
| 3,101,713 | 8/1963 | Sargent | 128/263 |
| 3,699,962 | 10/1972 | Hanke | 128/263 |
| 3,983,868 | 10/1976 | Ring | 128/263 |

Primary Examiner—Kyle L. Howell
Assistant Examiner—Michael H. Thaler
Attorney, Agent, or Firm—Richard A. Wise; Oistein J. Bratlie; Mandel E. Slater

[57] ABSTRACT

A tampon inserter is disclosed of the type in which an insertion tube is pulled outwardly, withdrawing it from the tampon, which is left behind in a body cavity. An easily-assembled three-piece construction is described, which includes an outer tube, a retainer for the tampon fixedly connected within the outer tube, and an insertion tube slidably interposed therebetween. A collar on the outer tube controls depth of insertion.

6 Claims, 12 Drawing Figures

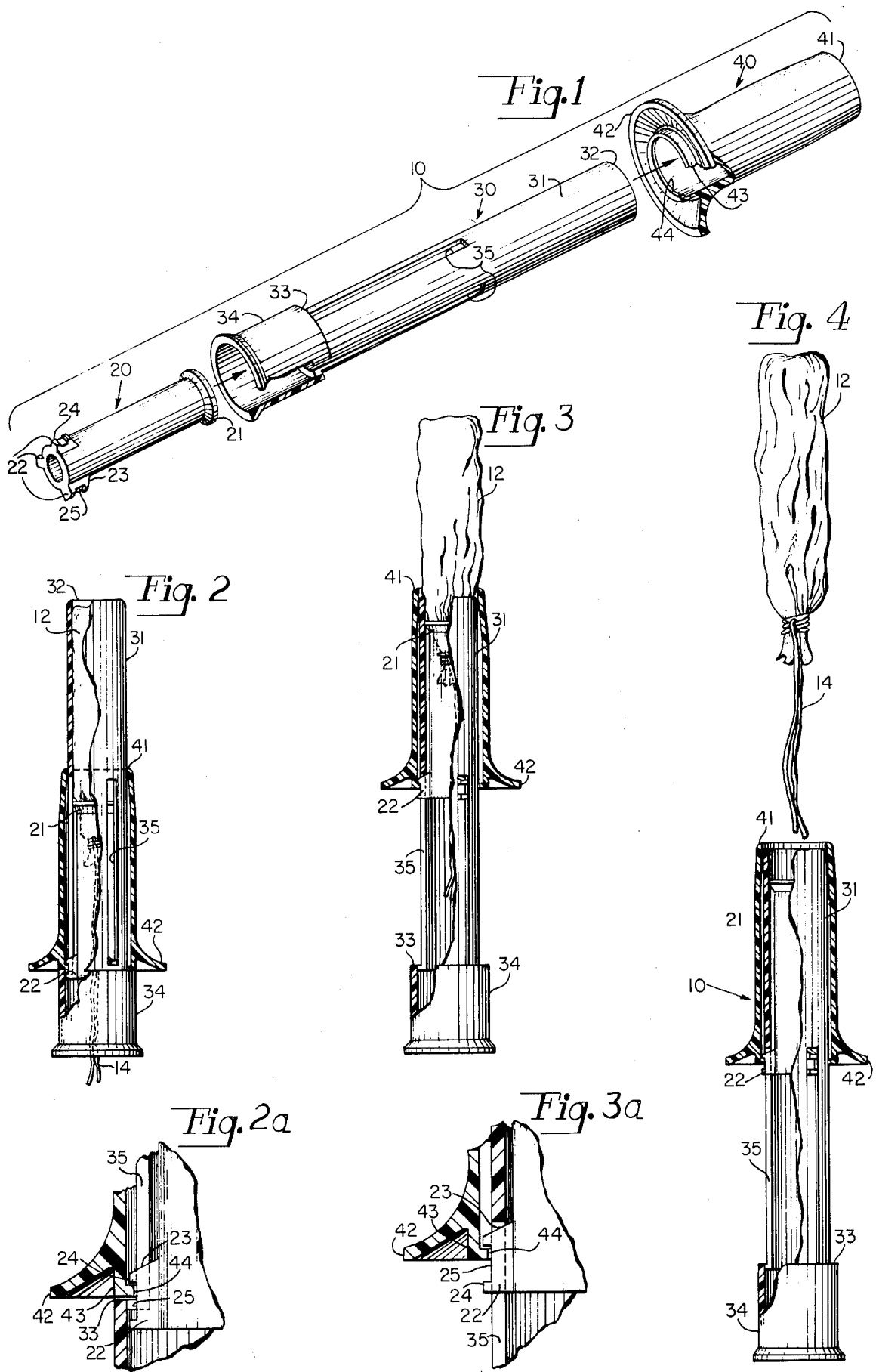

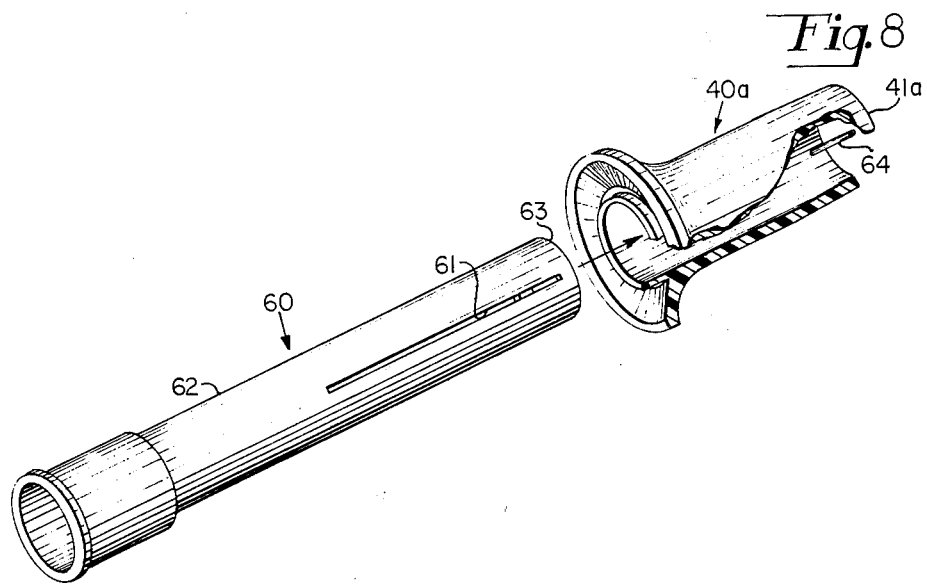
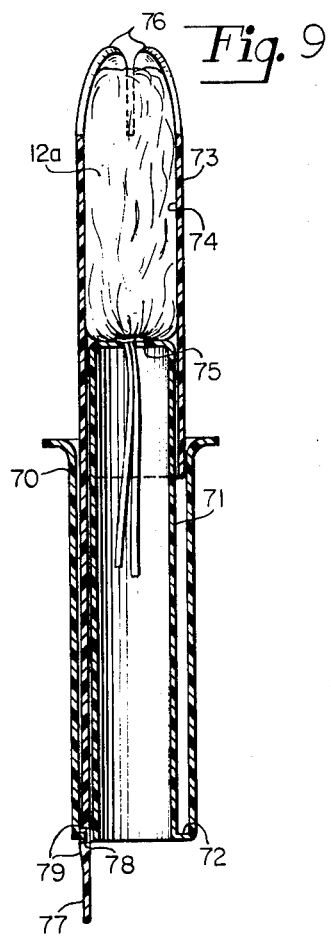
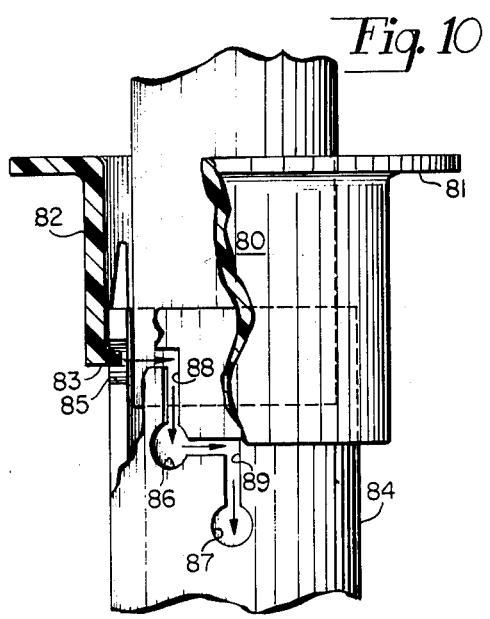

TAMPON INSERTER

BACKGROUND OF THE INVENTION

1. Field of the Invention

This invention relates to tampon inserters, and is directed more particularly to tampon inserters which deposit a tampon in a body cavity by pulling on, or withdrawing, the insertion tube.

2. Description of the Prior Art

In the field of tampon inserters there has come into wide use the kind of inserter which may be characterized as the "push" type. These inserters generally comprise, in a simple form, a pair of coaxial hollow cylinders or tubes, the larger outer tube serving as an insertion tube and containing a compressed tampon at its proximal end, and the smaller inner tube serving as a plunger, which, when operated from the distal end of the insertion tube and moved axially along the insertion tube toward its proximal end, ejects the tampon from the insertion tube. A plunger seat may be formed at the proximal end of the inner tube, to insure better engagement with the tampon and more positive ejection from the insertion tube, and suitable structure may be provided at the distal end of the insertion tube to provide gripping means and thereby facilitate use of the tampon inserter.

It has been recognized that tampon inserters of the type described above have certain deficiencies which are readily apparent to many users of such devices. An important shortcoming is the variation in depth of placement of the tampon within the vagina. If placement is too shallow, pressure from the sphincter muscles against the tampon can cause discomfort, and accidental expulsion of the tampon is a further possibility. If placement is too deep, the tampon may extend into portions of the vagina, where, for reasons of the size and shape of that organ, complete contact between the tampon and the walls of the vagina is not maintained; this can lead to the so-called "bypass" problem, in which menstrual fluids can get by the tampon without being absorbed.

Another deficiency of the "push" type inserter described above is the discomfort experienced by a substantial portion of users when the plunger is operated to eject the tampon from the insertion tube. Unlike the outer surface of the insertion tube, which is purposely made smooth and somewhat lubricious for easy and comfortable insertion, the tampon usually has a rough and irregular surface, in part as a consequence of its design for absorptive properties, and shoving it out of the insertion tube against the delicate walls and folds of the vagina is frequently accompanied by discomfort due to the friction.

Controlling depth of insertion has been addressed in U.S. Pat. No. 702,570, which issued on June 17, 1902, and more recently in U.S. Pat. No. 3,753,437, which issued on Aug. 21, 1973. In both patents there is provided an annular collar or shield around the insertion tube at the proper distance from the proximal end of the insertion tube, in order to control depth of penetration of the insertion tube and, consequently, depth of placement of the tampon. However, no solution is provided to the above-mentioned friction problem.

One solution to the friction problem is shown in U.S. Pat. No. 2,155,285, which issued on Apr. 18, 1939, in which a tampon inserter is provided of a kind that can be termed the "pull" type. After insertion of the appliance into a body cavity, an inner retainer portion, which is analogous to a plunger means, is held stationary while an outer cylinder, analogous to an insertion tube, is pulled away or withdrawn, leaving the tampon behind, in place. The friction problem is thereby overcome, since, instead of pushing the tampon out of the inserter, roughly shoving it against delicate body tissues, it is located in its final position at the time when the appliance is inserted and is not moved in or out relative to the vagina when the outer tube is withdrawn. However this approach provides no solution to the above-mentioned insertion depth problem, because the user is not provided with any positive stop means, but must instead endeavor to hold the plunger means in fixed position while withdrawing the outer tube, a procedure which is readily subject to error and inconsistency.

If the tampon inserter described in U.S. Pat. No. 2,155,285, referred to above, were provided with a collar or shield around the outer cylinder, near the distal end, for example, in an attempt to control depth of insertion, little additional benefit would be realized, because the collar would be withdrawn from place along with the outer tube, when it is needed instead to provide a stationary position reference until after the tampon is deposited in its correct position. It is also to be recognized that known tampon inserters of the push or pull type have an inherent similarity in that the push type, if the plunger is provided with a long enough handle to allow maintaining a positive grip on it throughout use, can be operated in the same manner as the pull type, by pulling back on the insertion tube while holding the plunger firmly in place, instead of pushing on the plunger while holding the insertion tube in place.

It will be seen, then, that each of the above types of tampon inserter has its own advantages and disadvantages, and that neither has heretofore combined in one type the desired properties of both without the shortcomings of either.

SUMMARY OF THE INVENTION

Accordingly it is the principal object of the present invention to provide a tampon inserter which provides consistently both proper depth of insertion and, at the same time, minimal discomfort from friction during insertion.

A further object of the invention is the provision of a tampon inserter which is simple in construction, with easily formed parts, conveniently assembled, and reliable in operation.

A still further object of the invention is the provision of a tampon inserter which is convenient and easy to use.

With the above and other objects in view a feature of the present invention is the provision of a tampon inserter of the "pull" type in which a retainer is fixedly connected within a stationary outer tube, with an insertion tube slidably interposed therebetween. A tampon, disposed within the insertion tube and resting against the fixed retainer, is left behind as the insertion tube is pulled back or withdrawn. The outer tube may be provided with a collar, serving as a positive stop to control insertion depth and thereby insure proper positioning of the tampon in a body cavity.

In a preferred embodiment of the invention the outer tube is provided with an integral collar, and an internal locking ring at its distal end, and the retainer includes a plurality of guide fingers, each with a locking groove cooperating with the locking ring on the outer tube to secure the retainer to the outer tube. The sliding insertion tube is provided with a plurality of guide slots cooperating with the guide fingers to guide and limit outward travel of the insertion tube, with inward travel limited by abutment of a handle portion of the insertion tube against the distal end of the outer tube. Alternatively the collar may be a separate part keyed into a choice of longitudinal slots of different length in the outer tube, in order to provide a choice of insertion depths to suit users of varying anatomical size.

In further embodiments of the invention the outer tube and retainer can be formed as a single piece, with sufficient connecting structure at their distal ends for structural integrity, but leaving one or more slots or openings in the connecting structure. An insertion tube is provided which has a short tubular portion at its proximal end just long enough to contain a tampon and also extend slightly beyond the tampon retainer seat, which also provides, together with the outer tube, a guideway for the insertion tube. The remainder of the insertion tube is formed into one or more elongated arms extending through and beyond the openings in the structure connecting outer tube and retainer, and providing a handle means for pulling on the insertion tube in the manner already described.

The retainer need only include sufficient structure to keep the tampon substantially forward of the outer tube, so that it can be left behind when the insertion tube is withdrawn. Consequently, it still further embodiments of the invention, directed toward a simplified construction, an internal rib may be used as a retainer, positioned adjacent the forward end of the outer tube.

The above and other features of the invention, including various novel details of construction and combinations of parts, will now be more particularly described with reference to the accompanying drawing and pointed out in the claims. It will be understood that the particular device embodying the invention is shown by illustration only and not as a limitation of the invention. The principles and features of this invention may be employed in various and numerous embodiments without departing from the scope of the invention.

BRIEF DESCRIPTION OF THE DRAWING

Reference is made to the accompanying drawing in which are shown illustrative embodiments of the invention from which its novel features and advantages will be apparent.

FIG. 1 is an exploded isometric view, partially broken away, of one form of tampon inserter illustrative of an embodiment of the invention;

FIG. 2 is an elevational view, partially in section, of the tampon inserter shown in FIG. 1, in closed position, prior to use;

FIG. 2a is a sectional view, on an enlarged scale, of a portion of the tampon inserter as shown in FIG. 2;

FIG. 3 is an elevational view, partially in section, of the tampon inserter shown in FIG. 1, in open, dispensing position;

FIG. 3a is a sectional view, on an enlarged scale, of a portion of the tampon inserter as shown in FIG. 3;

FIG. 4 is an elevational view, partially in section, of the tampon inserter shown in FIG. 1, after dispensing the tampon;

FIG. 8 is an exploded isometric view, partially broken away, of a simplified form of tampon inserter;

FIG. 9 is a sectional view of another form of tampon inserter according to the invention; and FIG. 10 is a view, partially broken away and on an enlarged scale, of an adjustable collar means for the tampon inserter of FIG. 9.

DESCRIPTION OF THE PREFERRED EMBODIMENTS

Figure 5:
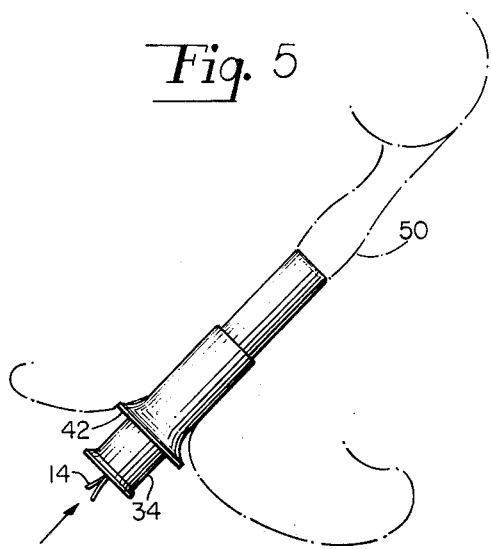
FIG. 5 is a sectional view, showing the tampon inserter in a body cavity, prior to dispensing the tampon.

Referring to the drawing and in particular to FIG. 1, it will be seen that the illustrative tampon inserter 10 includes a retainer 20, insertion tube 30, and outer tube 40, all of which may be of polyethylene.

Retainer 20 is an elongated element of generally tubular shape and is provided at its proximal end with a flange-like retainer seat 21 against which a tampon may rest. At the distal end of the retainer, equally spaced about its circumference, are three identical guide fingers 22, each having a forward edge in the form of a ramp 23 at an acute angle to the surface of the retainer, and an outer or top portion 24 with transversely extending locking groove 25 formed therein.

Insertion tube 30 includes a hollow cylindrical barrel 31, which has any otherwise sharp edges rounded off at its proximal end 32 (to avoid discomfort on insertion into a body cavity) and connected by a shoulder 33 to a hollow cylindrical handle 34, of larger diameter than barrel 31. Three equally-spaced guide slots 35 are formed in insertion tube 30, extending parallel to the axis of the insertion tube from about the midpoint of barrel 31 rearwardly through shoulder 33. The extension of guide slots 35 through shoulder 33 may best be seen with reference to FIGS. 1 and 2a.

Outer tube 40 is of generally tubular shape and is rounded at its forward end 41 (again, to minimize discomfort), but squared off at its distal end 43. A locking ring 44 (shown oversize for clarity) is formed internally of and flush with the distal end of outer tube 40, which also includes, adjacent distal end 43, structure flaring outwardly to form collar 42. A slight inward taper near forward end 41 of the outer tube is provided to have just enough clearance for a close sliding fit with barrel 31 of insertion tube 30.

The dimensions of the parts are such that retainer 20, including retainer seat 21, fits easily within barrel 31, and guide fingers 22 are received in guide slots 35, from which they protrude slightly to engage locking ring 44 of outer tube 40. Handle 34 is made large enough for the guide fingers to pass through easily and engage the guide slots. Barrel 31 and locking ring 44 are dimensioned so that the barrel can slide through the locking ring without binding. Inward travel of insertion tube 30 into tube 40 is limited by abutment of shoulder 33 against distal end 43 of the outer tube. Guide fingers 22 interfere with locking ring 44, so that when the locking ring is in engagement with locking grooves 25, the parts are firmly held together.

The tampon inserter may easily and conveniently be assembled by bringing the parts together as indicated by the arrows in FIG. 1. First, insertion tube 30 is inserted all the way into the tube 40 until shoulder 33 abuts distal end 43 of the outer tube, as best shown in FIG. 2a. Then retainer 20 is placed into the insertion tube where, unless guide fingers 22 already happen to be aligned with guide slots 35, the guide fingers will rest against the inside of shoulder 33. While maintaining a small insertion force, the retainer is rotated in either direction until the guide fingers and guide slots come into alignment, whereupon the guide fingers will enter the guide slots. With additional force on the retainer locking ring 44 is made to ride up ramps 23 until the locking ring snaps into locking grooves 25, now holding all three parts permanently together. In order to prevent the retainer from slipping past locking ring 44 during assembly, a suitable assembly fixture may be introduced into barrel 31 to provide a stop for the retainer and prevent override.

The tampon inserter is made ready for use by placement therein of a tampon 12, together with its associated withdrawal string 14. Such tampons are well known in the art and form no part of the present invention. Tampon 12 is held within insertion tube 30 with the end where string 14 is attached resting against retainer seat 21. The string extends back through tubular retainer 20 and out through handle 34.

In use outer tube 40 of the tampon inserter is held in fixed position, while insertion tube 30 is pulled back or withdrawn from around tampon 12, leaving the tampon behind, as best shown in FIGS. 3 and 4. When the insertion tube is pulled back, its outward travel is limited when the ends of the guide slots 35 come into abutment with ramps 23 on guide fingers 22, as may best be seen with reference to FIG. 3a. With locking ring 44 secured in locking grooves 25, the insertion tube can not be withdrawn further from the outer tube.

Figure 6:
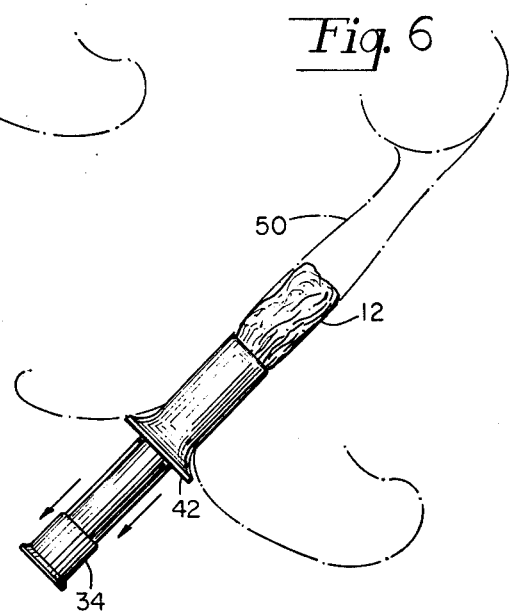
FIG. 6 is a view similar to FIG. 5, showing the tampon being deposited in a body cavity.
Figure 7:
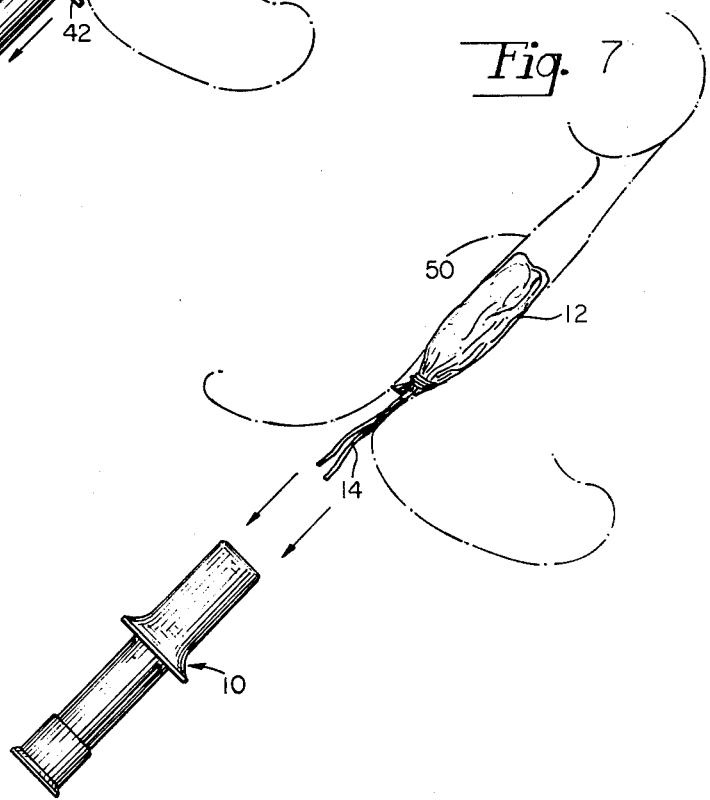
FIG. 7 is a view similar to FIG. 5, showing the tampon in place and the inserter withdrawn.

The use of tampon inserter 10 to place a tampon 12 within a body cavity may best be seen with reference to FIGS. 5–7. In FIG. 5 the tampon inserter has been placed within a body cavity 50 by manipulating handle 34 so as to push the tampon inserter into the body cavity until stopped by collar 42. In the embodiment shown a handle of generous size has been provided to facilitate and encourage proper use. Obtaining insertion by manipulating primarily the handle avoids a premature withdrawal of the insertion tube (of which the handle is a part) and deposition of the tampon in other optimal position. Proper deposition of the tampon is obtained as shown in FIG. 6, preferably with the user employing one or two fingers from one hand behind collar 42 to hold the tampon inserter in position, while using the other hand to pull back on handle 34, in the direction shown by the arrows. In FIG. 7 the tampon inserter has been withdrawn from the body cavity, leaving behind tampon 12 in optimum position and string 14 available for later withdrawal of the tampon.

The manner of using the tampon inserter serves to illustrate further advantages of the present invention. First, as has already been mentioned, the provision of collar 42 insures correct insertion depth every time, but the collar is not shoved against sensitive tissues as the tampon is deposited, as would be the case with inserters of the "push" type, but held in place by only such light finger pressure as is required to hold it while the insertion tube is pulled back. Another advantage is that the string is protected within the insertion tube as the tampon inserter is withdrawn from a body cavity, in contrast to the exposed string associated with tampon inserters of the "push" type, so that accidental pulling of the string during withdrawal is avoided.

A simplified tampon inserter construction is shown in FIG. 8, in which the retainer means is in the form of an internal rib, positioned adjacent the forward of the outer tube. In the embodiment of FIG. 8 the insertion tube 60 is similar to insertion tube 30, previously described, except that two narrow 180° -opposed guide slots 61 extend from about mid-way along barrel portion 62 to a point adjacent proximal end 63 of the insertion tube. Outer tube 40a is as previously described, and is additionally provided with an internal rib 64 adjacent forward end 41a of the outer tube. According to one method of assembly the rib is attached after insertion tube 60 has been fully inserted into outer tube 40a. In the assembled tampon inserter rib 64 extends through guide slots 61 to control sliding motion of the insertion tube relative to the outer tube. Rib 64 also serves as a retainer means holding a tampon substantially forward of the outer tube for deposition in a body cavity when the insertion tube is pulled back.

In the embodiment of FIG. 8 the retainer means is connected to the outer tube near the forward end of the outer tube, a design choice which requires that the guide slots in the insertion tube also be located in the forward portion, toward the proximal end, of the insertion tube, where they are not covered by the outer tube. It use, when the tampon inserter is inserted into a body cavity the exposed slots, if unduly large, can entrap flesh and cause discomfort. This difficulty may be avoided by minimizing the width of the guide slots and the dimensions of the retainer structure where it passes through those slots. Another way to avoid the above-mentioned difficulty is to use an elongated rib member providing a tampon retainer portion adjacent the forward end of the outer tube, which rib member nevertheless extends toward and is attached to the outer tube near its distal end; this arrangement has the guide slots extend more rearwardly along the barrel of the insertion tube where they will be shielded by the outer tube.

In the embodiment shown in FIG. 9 outer tube 70 and retainer 71 are formed as a single piece, connected by web 72. Insertion tube 73 has a tubular portion 74 extending over a portion of the retainer and enclosing a tampon 12a held between retainer seat 75 and converging end flaps 76. The remainder of the insertion tube is formed into a handle 77 extending through a complementary slot 78 in web 72. Detent means 79 helps prevent accidental movement of the insertion tube in either direction, in order to avoid either premature deposition of the tampon or falling out of the insertion tube. The detent may be intentionally overridden without difficulty, however, when the tampon inserter is used in the manner previously described.

In FIG. 10 there is shown a variation of the tampon inserter of FIG. 9, in which the collar portion of the outer tube is made as an additional, separate part, adjustable in position along the outer tube, in order to control depth of insertion for users of varying anatomical size. The collar 80 has a flange portion 81, tubular body portion 82 and inward-pointing key 83 formed in the body portion. The key fits into one of three holes 85, 86, 87 in outer tube 84, the holes being connected by slots 88, 89 to provide adjustable collar positions, selected by rotating and sliding the collar so that key 83 is maneuvered into one of the three holes. In like manner collar 42 in the embodiment of FIG. 1 (and, similarly, the collar portion in the embodiment of FIG. 8) can be made as a separate, adjustable part relative to the remainder of the outer tube structure, in order to provide adjustable depth of insertion.

While various aspects of the invention have been illustrated by the foregoing detailed embodiments, it will be understood that various substitutions of equivalents may be made without departing from the spirit and scope of the invention.

What is claimed is:

1. A tampon inserter of the pull type comprising an outer tube, an insertion tube slidable within said outer tube, and retainer means fixedly connected within said outer tube, said insertion tube including means permitting said retainer means to extend to the inside thereof while permitting free movement thereof, said insertion tube having a proximal end for insertion into a body cavity and adapted to contain a tampon between said proximal end and said retainer means, said retainer means so positioned that when said insertion tube is moved away from said body cavity, said retainer means engages said tampon to cause it to be deposited outside said tampon inserter in said body cavity.

2. A tampon inserter as defined in claim 1, and further including a collar around said outer tube, to control the depth to which said tampon inserter may be inserted within said body cavity.

3. A tampon inserter as defined in claim 2, and further including means for adjusting the position of said collar along said outer tube.

4. A tampon inserter as defined in claim 1, in which said means permitting said retainer means to extend to the inside thereof while permitting free movement thereof comprises a slot, and said retainer means comprises a rib extending through said slot.

5. A tampon inserter as defined in claim 1, in which said means permitting said retainer means to extend to the inside thereof while permitting free movement thereof comprises a slot, said retainer means comprises an elongated element having a proximal end adapted to engage said tampon, and said retainer means and said outer tube are connected by locking means extending through said slot.

6. A tampon inserter as defined in claim 1, in which said retainer means comprises an elongated element having a proximal end adapted to engage said tampon and is joined to said outer tube by a web, and said insertion tube includes handle means comprising at least one elongate portion extending through at least one corresponding opening formed in said web.

* * * * *